United States Patent [19]
Cole et al.

[11] 4,029,784
[45] June 14, 1977

[54] PYRIMIDINE SULFAMATE FUNGICIDES

[75] Inventors: Ann Mary Cole, Maidenhead; John Angus William Turner, Wokingham; Brian Kenneth Snell, Twyford, all of England

[73] Assignee: Imperial Chemical Industries Limited, London, England

[22] Filed: Feb. 13, 1975

[21] Appl. No.: 549,787

Related U.S. Application Data

[62] Division of Ser. No. 284,546, Aug. 29, 1972, Pat. No. 3,880,852.

[30] Foreign Application Priority Data

Sept. 23, 1971 United Kingdom ............ 44401/71

[52] U.S. Cl. ............................ 424/248.5; 424/244; 424/251
[51] Int. Cl.$^2$ ............................................ A01A 9/22
[58] Field of Search ............... 424/248, 251, 248.5

[56] References Cited

UNITED STATES PATENTS

| | | | |
|---|---|---|---|
| 3,493,574 | 2/1970 | Baranyouits et al. | 260/256.5 R |
| 3,676,443 | 7/1972 | Snell et al. | 260/256.5 R |
| 3,880,852 | 4/1975 | Cole et al. | 260/256.5 R |

FOREIGN PATENTS OR APPLICATIONS

| | | | |
|---|---|---|---|
| 1,185,039 | 2/1970 | United Kingdom | 260/247.1 M |
| 1,182,584 | 2/1970 | United Kingdom | 260/247.1 M |

*Primary Examiner*—Leonard Schenkman
*Attorney, Agent, or Firm*—Cushman, Darby & Cushman

[57] ABSTRACT

Pyrimidine derivatives are provided wherein the 6-position carries the group $OSO_2NR^5R^6$ and the 2-position carries the group $NR^1R^2$. $R^1$ and $R^2$ are preferably hydrogen or lower alkyl but both are not hydrogen and $R^5$ and $R^6$ are preferably lower alkyl, although these groups may form a cyclic ring. The 3-position and 4-position are preferably substituted with lower alkyl, although lower alkynyl or alkenyl may be used. The derivatives are compounded into compositions for combatting fungal pests.

26 Claims, No Drawings

PYRIMIDINE SULFAMATE FUNGICIDES

This is a division of application Ser. No. 284,546, filed Aug. 29, 1972, and now issued as U.S. Pat. No. 3,880,852.

This invention relates to new pyrimidine derivatives, to fungicidal compositions containing them and to methods of combating fungal pests using them.

In British Pat. No. 1,185,039 there are disclosed and claimed pyrimidine derivatives of the formula:

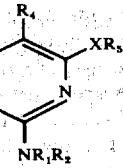

or a salt thereof, wherein $R_1$ and $R_2$ represent atoms of hydrogen, substituted or unsubstituted hydrocarbon groups, or together with the adjacent N-atom form a heterocyclic ring which may contain one or more additional hetero- atoms; $R_3$ and $R_4$ represent atoms of hydrogen or halogen, substituted or unsubstituted hydrocarbon groups, or nitro groups; X represents an atom of oxygen or sulphur; and $R_5$ is a carbonyl or sulphonyl group bearing directly, or through an oxygen or sulphur atom, a substituted or unsubstituted hydrocarbon group, or a heterocyclic group. These compounds are useful fungicides.

In the aforesaid British Pat. No. 1,185,039 there are therefore disclosed certain sulphonyl ester derivatives of pyrimidines. Only one sulphamyl ester was specified in that patent, however, having the structure:

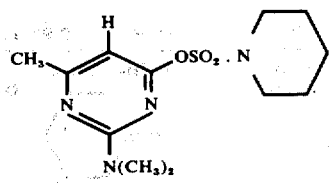

This compound does not fall within the narrow class of compounds defined by the present invention and does not possess the same pattern or level of fungicidal activity against powdery mildews.

In British Pat. No. 1,182,584 there are disclosed fungicidally active pyrimidine derivatives which are characterised in having a 6-hydroxy group (or a 6-mercapto group) and a 2-amino group present on the pyrimidine ring. These pyrimidine derivatives are highly active fungicides.

None of the compounds specifically disclosed in either of the two aforesaid British Patents, which represent the closest prior art, however, possess a high degree of activity against all the powdery mildews, and against apple powdery mildew *Podosphaera leucotricha* in particular, as is represented by the class of compounds defined by the present invention.

It has now been found that a narrow class of pyrimidines, some only of which fall within the broad class defined in British Pat. No. 1,185,039 but not specifically disclosed therein, are particularly broad spectrum fungicides and possess a higher level of activity against powdery mildews, especially against the powdery mildew of apple trees, *Podosphaera leucotricha*.

Accordingly the present invention provides a pyrimidine sulphamate derivative having the general formula:

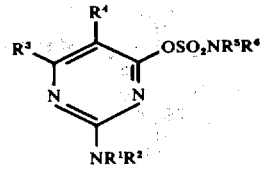

and salts thereof, wherein $R^1$ and $R^2$ are hydrogen or lower alkyl, lower alkynyl, or lower alkenyl but are not both hydrogen, or together with the adjacent N-atom form a heterocyclic group; $R^3$ and $R^4$ are lower alkyl, lower alkynyl, or lower alkenyl; and $R^5$ and $R^6$ are lower alkyl, lower alkynyl, or lower alkenyl; or together with the adjacent N-atom form a heterocyclic group.

By the terms lower alkyl, lower alkynyl, and lower alkenyl, are intended groups containing up to six carbon atoms. Thus such a group may be a straight or branched chain or cyclic alkyl group. Suitable alkyl groups include, for example, methyl, ethyl, propyl, and butyl, and these may be normal, iso or tertiary groups where appropriate. Suitable alkenyl and alkynyl groups include, for example, allyl, butenyl and propargyl.

Preferred alkyl and alkenyl groups, however, are those containing from 1 to 4 carbon atoms, and from 3 to 4 carbon atoms, respectively, and alkyl groups are preferred.

When $R^1$ and $R^2$ and $R^5$ and $R^6$ together with the adjacent N-atom constitute a heterocyclic group this may comprise any heterocyclic ring, substituted or unsubstituted, for example acridine, isothiazole, pyrrolidine, isoxazole, piperazine, piperidine, aziridine, thiazole, azocine, azepine, pyrrole, pyrazole, imidazole, pyrimidine, indole, pyrazine, quinoxoline and morpholine. Preferred heterocyclic groups, however, comprise monocyclic rings containing 5-, 6- or 7- ring atoms and preferred substituents thereon include, for example, alkyl groups, for example methyl groups.

In a preferred aspect, therefore, the invention provides a pyrimidine sulphamate derivative having the formula:

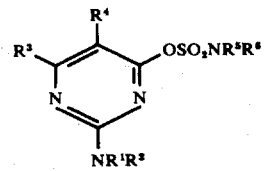

and salts thereof, wherein $R^1$ and $R^2$ are hydrogen or lower alkyl, but are not both hydrogen, or together with the adjacent N-atom form a heterocyclic group; $R^3$ and $R^4$ are lower alkyl; and $R^5$ and $R^6$ are lower alkyl or together with the adjacent N-atom form a monocyclic, 5-, 6- or 7- membered heterocyclic ring, optionally substituted.

Preferred compounds are those wherein $R^3$ is methyl; $R^4$ is n-butyl; $R^1$ and $R^2$ are hydrogen, allyl, methyl or ethyl but not both hydrogen; and $R^5$ and $R^6$ are methyl, ethyl, propyl or butyl or together with the adjacent N-atom form a pyrrole, piperidino, morpholino, piperazino or azepino ring, optionally substituted with methyl.

In a further aspect, therefore, the invention provides a pyrimidine sulphamate derivative having the formula:

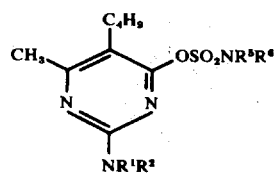

and salts thereof, wherein $R^1$ and $R^2$ are hydrogen, methyl, ethyl or allyl but are not both hydrogen; and $R^5$ and $R^6$ are methyl, ethyl, propyl or butyl or together with the adjacent N-atom form a pyrrolidino, morpholino, piperidino, piperazino or azepino ring, optionally substituted with methyl.

In some aspects it is preferred that $R^5$ and $R^6$ are lower alkyl groups, for example methyl, ethyl, propyl and butyl. In some experiments these compounds, especially those wherein $R^1$ and $R^2$ were also lower alkyl groups, displayed a slightly higher level of fungicidal activity.

In an even more preferred aspect the invention provides a pyrimidine sulphamate ester having the formula:

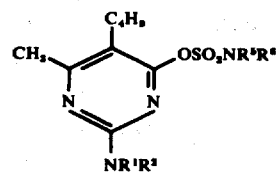

and acid addition salts thereof, wherein $R^1$ and $R^2$ are hydrogen, methyl or ethyl but are not both hydrogen; and $R^5$ and $R^6$ are methyl, ethyl, propyl or butyl.

Specific pyrimidine derivatives of the invention which have been found to be particularly useful are listed in the Table I below. The headings to the columns of the table correspond to the substituent groups on the pyrimidine ring in the general formula:

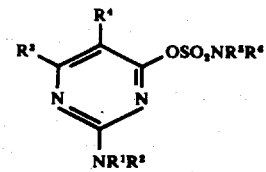

TABLE I

| Compound No: | $R^1$ | $R^2$ | $R^3$ | $R^4$ | $R^5$ | $R^6$ | Melting Point |
|---|---|---|---|---|---|---|---|
| 1 | $CH_3$ | $CH_3$ | $CH_3$ | $nC_4H_9$ | $CH_3$ | $CH_3$ | Oil |
| 2 | $CH_3$ | $CH_3$ | $CH_3$ | $nC_4H_9$ | —N(piperidino)— | | Oil |
| 3 | $CH_3$ | $CH_3$ | $CH_3$ | $nC_4H_9$ | —N(pyrrolidino)— | | Oil |
| 4 | $CH_3$ | $CH_3$ | $CH_3$ | $nC_4H_9$ | —N(morpholino)— | | Oil |
| 5 | H | $C_2H_5$ | $CH_3$ | $nC_4H_9$ | —N(piperidino)— | | 72° C |
| 6 | H | $CH_3$ | $CH_3$ | $nC_4H_9$ | —N(piperidino)— | | 114° C |
| 7 | H | $C_2H_5$ | $CH_3$ | $nC_4H_9$ | $nC_4H_9$ | $nC_4H_9$ | Oil |
| 8 | H | $C_2H_5$ | $CH_3$ | $nC_4H_9$ | $C_2H_5$ | $C_2H_5$ | Oil |
| 9 | $C_2H_5$ | $C_2H_5$ | $CH_3$ | $nC_4H_9$ | —N(piperidino)— | | 77° C |
| 10 | H | $nC_4H_9$ | $CH_3$ | $nC_4H_9$ | —N(piperidino)— | | 56° C |

TABLE I-continued

| Compound No: | R¹ | R² | R³ | R⁴ | R⁵ | R⁶ | Melting Point |
|---|---|---|---|---|---|---|---|
| 11 | H | nC₃H₇ | CH₃ | nC₄H₉ | —N (pyrrolidine ring) | | 60° C |
| 12 | —N (pyrrolidine ring) | | CH₃ | nC₄H₉ | —N (pyrrolidine ring) | | 88° C |
| 13 | H | iso-C₃H₇ | CH₃ | nC₄H₉ | —N (pyrrolidine ring) | | Oil |
| 14 | H | C₂H₅ | CH₃ | nC₄H₉ | isoC₄H₉ | isoC₄H₉ | Oil |
| 15 | H | C₂H₅ | CH₃ | n-C₄H₉ | CH₃ | CH₃ | Oil |
| 16 | H | C₂H₅ | CH₃ | n-C₄H₉ | isoC₃H₇ | isoC₃H₇ | Oil |
| 17 | H | C₂H₅ | CH₃ | nC₄H₉ | —N (4-methylpiperidine ring) —CH₃ | | 76–77° C |
| 18 | H | C₂H₅ | CH₃ | nC₄H₉ | nC₃H₇ | nC₃H₇ | Oil |
| 19 | H | C₂H₅ | CH₃ | nC₄H₉ | —N (7 ring) | | Oil |
| 20 | H | C₂H₅ | CH₃ | nC₄H₉ | —N (piperidine ring) | | 102–103° |
| 21 | H | C₂H₅ | CH₃ | nC₄H₉ | —N (piperazine) N—CH₃ | | Oil |
| 22 | H | C₂H₅ | CH₃ | nC₄H₉ | CH₃ | nC₄H₉ | Oil |
| 23 | H | C₂H₅ | CH₃ | nC₄H₉ | —N (morpholine ring) O | | mpt 103–104° |
| 24 | H | C₂H₅ | CH₃ | nC₄H₉ | CH₃ | —C₂H₅ | Oil |
| 25 | H | —CH₂.CH:CH₂ | CH₃ | isoC₄H₉ | CH₃ | CH₃ | 81° |
| 26 | H | —CH₂.CH:CH₂ | CH₃ | —CH₂.CH:CH₂ | CH₃ | CH₃ | 82° |
| 27 | H | —CH₂.CH:CH₂ | CH₃ | —CH₂.C:CH | CH₃ | CH₃ | mpt 62.64° |

For compounds recorded as "oils" in Table I elemental analyses were carried out. The results are as follows:

| | Required | | | Found | | |
|---|---|---|---|---|---|---|
| Compound No. | C | H | N | C | H | N |
| 1 | 49.35 | 7.59 | 17.73 | 49.18 | 6.96 | 17.82 |
| 2 | 53.92 | 7.86 | 15.73 | 53.94 | 8.53 | 15.10 |
| 8 | 52.3 | 8.14 | 16.28 | 52.44 | 7.97 | 16.11 |
| 15 | 49.5 | 7.6 | 17.7 | 48.0 | 7.37 | 17.5 |
| 18 | 54.5 | 8.60 | 15.06 | 55.02 | 8.60 | 14.5 |
| 19 | 55.1 | 8.1 | 15.14 | 53.9 | 7.92 | 13.92 |
| 22 | 53.60 | 8.38 | 15.64 | 53.52 | 8.41 | 15.89 |
| 23 | 50.30 | 7.26 | 15.64 | 51.10 | 7.34 | 16.00 |
| 24 | 50.93 | 7.88 | 16.98 | 50.88 | 7.69 | 16.70 |
| 4 | 50.30 | 7.26 | 15.64 | 49.95 | 7.41 | 15.25 |
| 7 | 57.00 | 9.00 | 14.00 | 56.35 | 8.91 | 13.57 |
| 14 | 57.00 | 9.00 | 14.00 | 56.92 | 9.30 | 13.61 |
| 16 | 54.80 | 8.60 | 15.06 | 54.94 | 8.59 | 14.62 |
| 25 | 51.20 | 7.37 | 17.06 | 50.60 | 7.08 | 16.99 |
| 26 | 49.98 | 6.45 | 17.93 | 49.34 | 6.29 | 17.59 |
| 27 | 50.30 | 5.84 | 18.05 | 49.14 | 5.57 | 17.95 |

Compounds Nos. 1, 3, 5, 8, 11 and 15 are particularly useful fungicides.

The invention, therefore, includes, as new compounds, each and every specific pyrimidine sulphamate derivative set out in Table I above, and in particular, Compound Nos. 1, 3, 5, 8, 11 and 15.

In this specification the numbering of the pyrimidine ring is as follows:

It may be noted that the 4- and 6- positions are equivalent.

The pyrimidine sulphamate derivatives of the invention may be made by reacting the appropriate 6-hydroxypyrimidine with the appropriate sulphamoyl chloride. The 6-hydroxypyrimidine may be prepared by any of the methods set out in the literature and in British Patent 1182584 and British Pat. Application No. 33079/72. The 6-hydroxypyrimidine is treated with alkali metal hydroxide, for example sodium hydroxide, in an organic liquid, for example toluene, benzene, xylene or ethyl acetate and the water removed by subjecting the mixture to reflux. Having thus formed the sodium salt of the pyrimidine, the sulphamoyl chloride is added and heating under reflux continued. The reaction mixture is then extracted with caustic, for example with 10% NaOH, to remove unchanged 6-hydroxypyrimidine and then washed with water until neutral washings (to litmus) are obtained. A recrystallisation, or other purification procedure, may then be carried out if necessary, or if desired.

As an alternative to the above procedure, the 6-hydroxypyrimidine may be reacted with alkali metal or sodium methoxide or ethoxide in methanol or ethanol, thereafter removing the alcohol used as solvent and adding the sulphamoyl chloride. Thereafter the reaction is carried forward as described above.

Molar proportions of reactants are preferably used.

As suitable salts of the pyrimidine derivatives of this invention there may be mentioned, for example, the hydrochlorides. Other salts include the salts of the pyrimidine derivatives with organic acids, for example, acetates, picrates, and the like. These salts may be prepared quite readily, in the usual way, by adding the appropriate acid to the pyrimidine sulphamate.

The compounds of the invention are, as previously mentioned, active fungicides, particularly useful against the diseases:

*Sphaerotheca fuliginea* (powdery mildew) on cucumber
*Podosphaera leucotricha* (powdery mildew) on apple
*Uncinula necator* (powdery mildew) on vine
*Erysiphe graminis* (powdery mildew) on barley
*Erysiphe graminis* (powdery mildew) on wheat The compounds may be used as such for anti-fungal purposes but are more conveniently formulated into compositions for such usage.

In a further aspect, therefore, this invention provides a fungicidal composition comprising as an active ingredient a pyrimidine sulphamate having the formula:

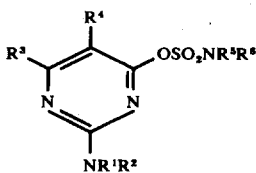

or a salt thereof, wherein $R^1$ and $R^2$ are hydrogen or lower alkyl, lower alkynyl or lower alkenyl but are not both hydrogen, or together with the adjacent N-atom form a heterocyclic group; $R^3$ and $R^4$ are lower alkyl, lower alkynyl or lower alkenyl; and $R^5$ and $R^6$ are lower alkyl, lower alkynyl or lower alkenyl or together with the adjacent N-atom form a heterocyclic group; and a carrier for the active ingredient.

In a preferred aspect the invention provides a fungicidal composition comprising, as an active ingredient, a pyrimidine sulphamate derivative having the formula:

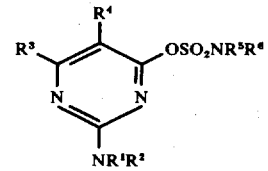

or a salt thereof, wherein $R^1$ and $R^2$ are hydrogen or lower alkyl, but are not both hydrogen, or together with the adjacent N-atom form a heterocyclic group; $R^3$ and $R^4$ are lower alkyl; and $R^5$ and $R^6$ are lower alkyl or together with the adjacent N-atom form a monocyclic 5-, 6- or 7- membered heterocyclic ring, optionally substituted; and a carrier for the active ingredient.

In a more preferred aspect the invention provides a fungicidal composition comprising, as an active ingredient a pyrimidine sulphamate derivative having the formula:

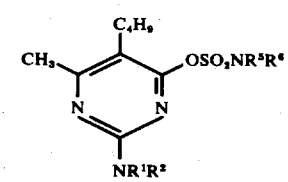

or a salt thereof, wherein $R^1$ and $R^2$ are hydrogen, methyl, ethyl, or allyl, but are not both hydrogen; and $R^5$ and $R^6$ are methyl, ethyl, propyl or butyl or together with the adjacent N-atom form a pyrrolidino, morpholino, piperidino, piperazino or azepino ring, optionally substituted with methyl; and a carrier for the active ingredient.

More particularly, in an especially preferred aspect, the invention provides a fungicidal composition comprising, as an active ingredient a pyrimidine sulphamate ester having the formula:

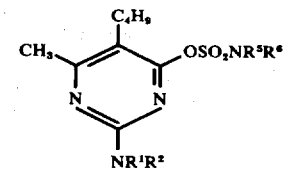

or an acid addition salt thereof, wherein $R^1$ and $R^2$ are hydrogen, methyl or ethyl but are not both hydrogen; and $R^5$ and $R^6$ are methyl, ethyl, propyl or butyl; and a carrier for the active ingredient.

The invention compounds and compositions containing them, are, as stated above, useful for combating fungal diseases.

In a further aspect, therefore, the invention includes a method for combating fungi which comprises treating plants, seeds or trees with a pyrimidine sulphamate derivative as hereinbefore defined in any of the preceding paragraphs, or a composition containing said pyrimidine derivatives as defined in any of the preceding paragraphs or hereinafter.

The active pyrimidine sulphamate derivatives of this invention, and compositions containing them, can be used to combat plant fungi and treat plants or seeds in a number of ways. Thus they can be applied, formulated or unformulated, directly to the foliage of a plant which is infected or likely to become infected. They can be applied also to bushes and trees, to seeds or to other propagative parts of plants, or to soil or other medium in which plants, bushes or trees are growing or to be planted. They can be sprayed on, dusted on or applied as a cream or paste formulation. Application can be to any part of the plant, bush or tree for example to the foliage, stems, branches or roots. All these modes of application are deemed to fall with the scope of the term "treating" used in this specification and claims, and the word "plant" is to be taken to include seedlings, bushes and trees. Furthermore, as is evident from the foregoing, the invention includes preventative, protectant, prophylactic and eradicant treatment.

The pyrimidine derivatives of this invention are preferably used in the form of compositions and these compositions may be used for agricultural and horticultural purposes. The type of composition used in any instance will depend upon the particular purpose for which it is to be used.

The compositions may be in the form of dusting powders or granules wherein the active ingredient is mixed with a solid diluent or carrier. Suitable solid diluents or carriers may be, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent assisting the adhesion of the composition to the seed, for example a mineral oil.

The compositions may also be in the form of dispersible powders or grains comprising, in addition to the active ingredient, a wetting agent to facilitate the dispersion of the powder or grains in liquids. Such powders or grains may include fillers, suspending agents and the like.

The aqueous dispersions or emulsions may be prepared by dissolving the active ingredient or ingredients in an organic solvent which may contain one or more wetting, dispersing or emulsifying agents and then adding the mixture so obtained to water which may likewise contain one or more wetting, dispersing or emulsifying agents. Suitable organic solvents are ethylene dichloride, isopropyl alcohol, propylene glycol, diacetone alcohol, toluene, kerosene, methylnaphthalene, xylenes and trichloroethylene.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example for improving the distribution, adhesive power and resistance to rain on treated surfaces, the different compositions can be better adapted for the various uses for which they are intended.

The pyrimidine derivatives may also be conveniently formulated by admixing them with fertilizers. A preferred composition of this type comprises granules of fertilizer material incorporating, for example coated with, a pyrimidine derivative. The fertilizer material may, for example, comprise nitrogen or phosphate-containing substances.

In yet a further aspect of the invention, therefore, we provide a fertilizer composition comprising a pyrimidine derivative as hereinbefore defined.

The compositions may also be in the form of liquid preparations to be used as dips or sprays which are generally aqueous dispersions or emulsions containing the active ingredient in the presence of one of more wetting agents, dispersing agents, emulsifying agents or suspending agents.

Wetting agents, dispersing agents and emulsifying agents may be of the cationic, anionic or non-ionic type. Suitable agents of the cationic type include, for example, quaternary ammonium compounds, for example, cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropyl-naphthalene sulphonic acids. Suitable agents of the nonionic type include, for example, the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins.

Suitable suspending agents are, for example, hydrophilic colloids, for example polyvinylpyrrolidone and sodium carboxymethylcellulose, and the vegetable gums, for example gum acacia and gum tragacanth.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage to be capable of dilution with water in order to form aqueous preparations which remain homogeneous for a sufficient time to enable them to be applied by conventional spray equipment. The concentrates may conveniently contain from about 10–85% by weight of the active ingredient or ingredients and generally from about 25–60% by weight of the active ingredient or ingredients. When diluted to form aqueous preparations, such preparations may contain varying amounts of the active ingredient or ingredients depending upon the purpose for which they are to be used, but an aqueous preparation containing from between 0.001 and 0.01% up to approximately 10% by weight of active ingredient or ingredients may be used.

It is to be understood that the biologically active compositions of this invention may comprise, in addition to a pyrimidine derivative, one or more other compounds having biological activity. They may also incorporate one or more stabilizing agents, for example epoxides, for example epichlorhydrin.

This invention is illustrated by the following Examples, those numbered 1 to 5 exemplifying methods of preparing the pyrimidine compounds listed in Table I above, while those numbered 6 to 12 are illustrative of compositions containing various of the pyrimidine derivatives as active ingredient.

EXAMPLE 1

This example illustrates the preparation of 5-n-butyl-2-dimethylamino-6-methyl-4-pyrimidinyl-1-pyrrolidine sulphonate, having the formula:

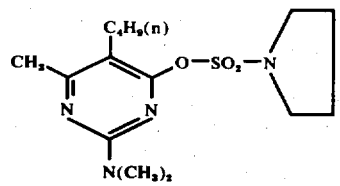

(Compound No. 3 of Table I)

To a solution of sodium ethoxide, prepared by dissolving sodium (43.3 g) in ethanol (1340 ml.) was added 5-n-butyl-2-dimethylamino-4-hydroxy-6-methylpyrimidine (392.1 g). The ethanol was then removed by distillation and replaced by dry ethyl acetate, part of which was distilled off to remove the last traces of ethanol. To the resultant mixture 1-pyrrolidine sulphonyl chloride (300 g) was added and the mixture refluxed for several hours. After cooling and filtering off the insoluble portion, the filtrate was washed with 5% sodium hydroxide solution and then with water until neutral washings were obtained.

After drying over anhydrous sodium sulphate the volatile fraction was removed by evaporation under reduced pressure, last traces of solvent being removed by heating to 80° C under high vacuum. The residual undistillable oil is 5-n-butyl-2-dimethylamino-6-methyl-4-pyrimidinyl-1-pyrrolidine sulphonate.

Compounds Nos. 2, 4, 9, 10, 11, 12, 17, 19, 20, 21 and 23 were prepared in an analogous manner using the appropriate reactants.

EXAMPLE 2

By a similar procedure to that illustrated in Example 1 above but using the appropriate reactants there was also obtained 5-n-butyl-2-ethylamino-6-methyl-4-pyrimidinyl-1-pyrrolidine sulphonate having the formula:

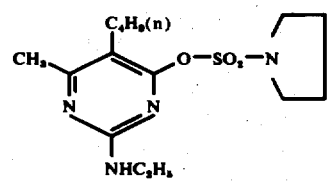

(Compound No. 5 of Table I)

EXAMPLE 3

In a similar experiment to that illustrated in Example 1, but using the appropriate reactants, and also using Toluene to assist in the removal of the last ethanol traces before adding the ethyl acetate, there was obtained 5-n-butyl-2-n-propylamino-6-methyl-4-pyrimidinyl-1-pyrrolidine sulphonate having the formula:

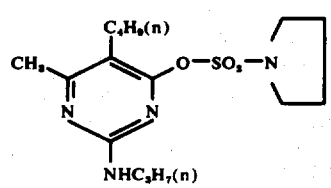

(Compound No. 11 of Table I)

EXAMPLE 4

This example illustrates the preparation of the compound having the structure:

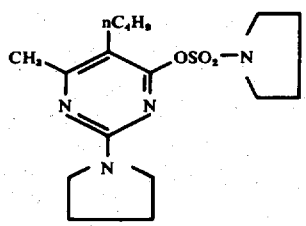

(Compound No. 14 of Table I)

Sodium (1.15 g) was dissolved in ethanol (100 ccs) and the pyrimidine, 2-pyrollidine-4-methyl-5-nbutyl-6-hydroxypyrimidine (11.77 g., 0.05M), added and allowed to dissolve. The solution was then evaporated to dryness. The resulting solid was suspended n benzene and 1-pyrrolidine sulphonyl chloride (8.48 g., 0.05M) added. The mixture was then heated under reflux for 2½ hours, allowed to cool and filtered. The filtrate was then washed with water, 10% sodium hydroxide solution and then with portions of water, until the washings gave a neutral reaction. The product was then dried over magnesium sulphate, the magnesium sulphate filtered off and the solution stripped to dryness. Yield of product 10.79 g. (58.6%), melting point 88° C.

EXAMPLE 5

This example illustrates the preparation of the compound having the formula:

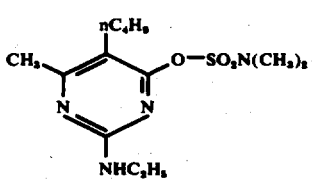

(Compound No. 15 of Table I)

2-ethylamino-4-methyl-5-n-butyl-6-hydroxypyrimidine (32.1 g; 0.11M) and sodium hydroxide (4.0 g; 0.1M) were mixed in toluene (300 ml) and the mixture heated under reflux to remove the water formed during the preparation of the sodium salt of the 6-hydroxy pyrimidine. Dimethylsulphamoyl chloride (14.35 g; 0.1M) in toluene (40 ml) was added and the whole mixture was heated under reflux for 3½ hours, and then cooled. The solution was washed three times with sodium hydroxide solution (200 ml. of a 10% solution) and then twice with water (200 ml). The solution was then dried with anhydrous magnesium sulphate and the toluene distilled off to yield a dark brown oil, yield 22.15 g. (70%) refractive index $n_D^{20}$ 1.5146.

The compounds numbered 1, 7, 8, 14, 15, 16, 18, 22 and 24 in Table I were prepared in an exactly analogous manner using the appropriate substituted pyrimidine and the appropriately substituted sulphamoyl chloride.

EXAMPLE 6

A dispersible powder formulation was made by mixing together the ingredients set out below and then grinding the mixture until all the constituents were thoroughly mixed.
  Compound No. 3 of Table I — 25%
  "AEROSOL" OT/B — 2%
  "Dispersol" A.c. — 5%
  China Clay — 28%
  Silica — 40%

EXAMPLE 7

This example illustrates the preparation of two dispersible powder formulations. In each instance all the ingredients are mixed in the proportions stated and the mixture then ground in a comminution mill.
  Compound No. 8 of Table I — 25%
  "PERMINAL" BX — 1%
  "Dispersol" T — 5%
  Polyvinylpyrrolidone — 10%
  Silica — 25%
  China Clay — 34%

Exactly the same formulation was made using Compound No. 15 of Table I.

EXAMPLE 8

The ingredients set out below were formulated into a dispersible powder by mixing and grinding the ingredients in the proportions stated.
  Compound No. 5 of Table — 25%
  "AEROSOL" OT/B — 2%
  "Dispersol" A — 5%
  China Clay — 68%

Exactly the same formulation was prepared using Compound No. 11 of Table I instead of Compound No. 5.

The following constitutes an explanation of the compositions or substances represented by the various Trade Marks and Trade Names referred to in the foregoing Examples.

LUBROL L is a condensate of 1 mole of nonyl phenol with 13 molar proportions of ethylene oxide.
AROMASOL H is a solvent mixture of alkylbenzenes
DISPERSOL T and AC is a mixture of sodium sulphate and a condensate of formaldehyde with the sodium salt of naphthalene sulphonic acid.
LUBROL APN 5 is a condensate of 1 mole of nonyl phenol with 5½ moles of naphthalene oxide.
CELLOFAS B 600 is a sodium carboxymethyl cellulose thickener.
LISSAPOL NX is a condensate of 1 mole of nonyl phenol with 8 moles of ethylene oxide.
AEROLSOL OT/B is dioctyl sodium sulphosuccinate.
PERMINAL BX is an alkyl naphthalene sulphonate (sodium salt)

EXAMPLE 9

The compounds of this invention were tested against a variety of foliar fungal diseases of plants. The technique employed is to spray foliage of the undiseased plants with a solution of the test compound. All solutions for spraying and drenching contained 100, 25, 10, 5 and 1 parts per million of the test compound. The plants were then infected with the diseases it was desired to control and after a period of days, depending upon the particular disease, the extent of the disease was visually assessed. The results are given in Tables 2A and 2B below, wherein the extent of the disease is given in the form of a grading as follows:

| Grading | Percentage Amount of Disease |
| --- | --- |
| 0 | 61 to 100 |
| 1 | 26 to 60 |
| 2 | 6 to 25 |
| 3 | 0 to 5 |

In Table 2 the disease is given in the first column, and in the second column is given the time which elapsed between infecting the plants and assessing the amount of disease.

TABLE 2

| Disease and Plant | Time Interval (days) | Disease Code Letter (Table 2A) |
| --- | --- | --- |
| Uncinula necator (Vine) | 10 | A |
| Erysiphe graminis (Wheat) |  | B |
| Podosphaera leucotricha (Apple) | 10 | C |
| Sphaerotheca fuliginea (Cucumber) |  | D |

TABLE 2A (100 ppm)

| Compound No. (Table I) | Disease Code Letter | | | |
| --- | --- | --- | --- | --- |
|  | A | B | C | D |
| 1 | 3 | 3 | 3 | 3 |
| 2 | 3 | 1 | 3 | 3 |
| 3 | 3 | 3 | 3 | 3 |
| 4 | 3 | 0 | 3 | 3 |
| 5 | 3 | 3 | 3 | 3 |
| 6 | 3 | 2 | 3 | 3 |
| 7 | 0 | — | 3 | — |
| 8 | 3 | — | 3 | 3 |
| 9 | 3 | 3 | 3 | 3 |
| 10 | 3 | 3 | 3 | 3 |
| 11 | 3 | 3 | 3 | 3 |
| 12 | 3 | 3 | 3 | 3 |
| 13 | 3 | 3 | 3 | 3 |
| 14 | 3 | 0 | 3 | 3 |
| 15 | 2 | — | 3 | 3 |
| 16 | 1 | — | 3 | 3 |
| 17 | 0 | — | 2 | 3 |
| 18 | 3 | — | 3 | 3 |
| 19 | 0 | — | 3 | 3 |
| 20 | 2 | — | 3 | 3 |
| 21 | 0 | — | 1 | 3 |
| 22 | 2 | — | 3 | 3 |
| 23 | 3 | — | 3 | 3 |
| 24 | 3 | — | 3 | 3 |

"—" means not tested.

The above results clearly show that the invention compounds are active against a range of powdery mildews.

In Table 2B below even lower rates of application (ppm-parts per million) are used and a comparison is made with earlier pyrimidine fungicides which themselves are firmly established commercial products (fungicides).

TABLE 2B (25, 10, 5 and 1 ppm)

| Compound No. | Rate of Application (ppm) | DISEASE | | |
| --- | --- | --- | --- | --- |
|  |  | Apple Powdery Mildew | Vine Powdery Mildew | Cucumber Powdery Mildew |
| 9 | 25 | 3 | 3 | 3 |
|  | 10 | 3 | 0 | 3 |
|  | 5 | 1 | 0 | 3 |

-continued

TABLE 2B (25, 10, 5 and 1 ppm)

| Compound No. | Rate of Application (ppm) | Apple Powdery Mildew | Vine Powdery Mildew | Cucumber Powdery Mildew |
|---|---|---|---|---|
| 11 | 25 | 3 | 3 | 3 |
|  | 10 | 3 | 3 | 3 |
|  | 5 | 3 | 1 | 3 |
| 10 | 25 | 3 | 3 | 3 |
|  | 10 | 3 | 3 | 3 |
|  | 5 | 1 | 1 | 3 |
| 3 | 25 | 3 | 1 | 3 |
|  | 10 | 3 | — | — |
|  | 5 | 3 | — | 2 |
| 5 | 25 | 3 | 3 | 3 |
|  | 10 | — | — | — |
|  | 5 | 3 | 3 | 3 |
|  | 1 | 3 | 2 | 2 |

TABLE 2B (cont) (25, 10, 5 and 1 ppm)

| Compound No. | Rate of Application (ppm) | Apple Powdery Mildew | Vine Powdery Mildew | Cucumber Powdery Mildew |
|---|---|---|---|---|
| 6 | 25 | 3 | 0 | 3 |
|  | 10 | 2 | 0 | 3 |
|  | 5 | 2 | 0 | 2 |
|  | 1 | — | — | — |
| 8 | 25 | 3 | 3 | 3 |
|  | 10 | 3 | 0 | 3 |
|  | 5 | 3 | — | 3 |
|  | 1 | — | — | — |
| Dimethirimol* | 25 | 2 | 0 | 3 |
|  | 10 | — | — | 3 |
|  | 5 | 1 | 0 | 3 |
|  | 1 | 0 | — | 1 |
| Ethirimol* | 25 | 3 | 0 | 3 |
|  | 10 | — | — | 2 |
|  | 5 | 0 | 0 | 2 |
|  | 1 | 0 | — | 1 |
| 2 | 25 | 3 | — | 3 |
|  | 10 | 3 | — | 3 |
|  | 5 | 3 | — | 1 |
| 4 | 25 | 3 | — | 3 |
|  | 10 | — | — | — |
|  | 5 | 3 | — | 1 |
| 12 | 25 | 3 | — | 3 |
|  | 10 | 2 | — | — |
|  | 5 | 1 | — | — |
| 15 | 25 | 3 | 3 | 3 |
|  | 10 | — | 1 | 1 |
|  | 5 | 3 | 1 | 1 |
| 18 | 25 | 3 | 0 | 3 |
|  | 10 | — | — | — |
|  | 5 | 1 | 0 | 0 |
| 20 | 25 | 2 | 2 | 3 |
|  | 10 | — | — | — |
|  | 5 | 1 | 1 | 2 |
| 22 | 25 | 3 | 1 | 3 |
|  | 10 | — | — | — |
|  | 5 | 1 | 0 | 1 |
| 23 | 25 | 3 | 3 | 3 |
|  | 10 | — | — | — |
|  | 5 | 0 | 0 | 1 |
| 24 | 25 | 3 | 2 | 3 |
|  | 10 | — | — | — |
|  | 5 | 2 | 2 | 0 |

*Dimethirimol and Ethirimol are compounds Nos. 4 and 30 respectively of Table 1 of U.K. Patent 1182584.

The above results clearly show the invention compounds to be more widely active, i.e. active against a wider range of powdery mildews at lower rates of applications, than the already excellent and commercially well-known pyrimidine fungicides of British Patent Number 1182584.

EXAMPLE 10

The improvement which the fungicidal compounds of the present invention represent over other well-established commercial products are demonstrated in a series of comparative tests described below.

In these tests the following commercial products are referred to:

| Common Name | Trade Name | Formula |
|---|---|---|
| DINOCAP | "CROTOTHANE" "KARATHANE" | See Page 192 of the "Pesticide Manual" second edition by Hubert Martin (1971) and published by the British Crop Protection Council. |
| BENOMYL | "BENLATE" | See Page 34 of the "Pesticide Manual" second edition by Hubert Martin (1971) and published by the British Crop Protection Council. |
| CELA 524 W | | HOCHNHCN⟨ring with two $CCl_3$ groups⟩NCHNHCOH |

A series of field trials were carried out comparing the invention compounds with well-known commercial products used for combating apple powdery mildew.

In each instance young fruiting apple trees were high volume sprayed (i.e. above the rate of 100 liters per hectare) to the point of run-off (that is until the leaves were well wetted and the spray fluid just started to run off the leaves). at approximately fortnightly intervals from bud burst until extension growth ceased in the Autumn (normally 9–10 sprays per season) with a formulation containing an invention compound. The trees were periodically assessed for mildew control by visual inspection of the leaves after the first appearance of mildew. Both primary and secondary mildew were observed.

TRIAL SERIES NO. 1 (U.K. 1972)
Primary Mildew Sporulation (% disease control)

| Compound | Rate of Application (ppm) | Mean of 6 Assessments | |
|---|---|---|---|
| DINOCAP (Karathane liquid) | 300 | 23.5 | |
| No. 5* (Table I) | 250 | 34.6 | |
| | 500 | 44.8 | |
| No. 11* (Table I) | 250 | 41.8 | |
| | 500 | 51.6 | |
| No. 5** | 250 | 39.0 | Two Assessments only |
| (Table I) | 500 | 55.4 | " |
| BENOMYL | 250 | 60.2 | " |
| CELA 524 W | 250 | 13.1 | " |

* Dispersible Powder Formulations
**Emulsifiable Concentrate Formulations.

Secondary Mildew (Percentage Mildew Control)

| Compound | Rate of Application | 1st (15.6.72) | 2nd (4.7.72) | 3rd (27.7.72) |
|---|---|---|---|---|
| DINOCAP | 300 | 46.4 | 18.4 | 11.6 |
| 5* (Table I) | 250 | 65.1 | 29.4 | 21.0 |
| | 500 | 54.0 | 45.0 | 44.6 |
| 11* (Table I) | 250 | 52.7 | 45.4 | 36.8 |
| | 500 | 59.4 | 49.0 | 50.2 |
| 5** (Table I) | 250 | 61.0 | 57.8 | 49.0 |
| | 500 | 83.6 | 75.9 | 72.0 |
| BENOMYL | 250 | 59.5 | 47.3 | 48.0 |
| CELA 524W | 250 | 78.0 | 71.3 | 43.4 |

*Dispersible Powder Formulations
**Emulsifiable Concentrate Formulations

The above results clearly show the superiority of the invention compounds over certain well-known products for combating Podosphaera leucotricha (apple powdery mildew) and their at least equal, or in some instances better, performance compared with the very best known commercially available apple mildew fungicides (for example Benomyl or BENLATE)

(a) Variety : Golden Delicious. (U.K. 1972)

| Compound | % Number of leaves with Secondary Mildew | Rate of Application |
|---|---|---|
| DINOCAP | 19.3 | 300 ppm |
| No. 5* | 16.4 | 250 ppm |
| No. 8* " | 15.0 | 250 ppm |
| No. 15* | 8.4 | 250 ppm |

(b) Variety : Cox's orange Pippin (U.K. 1972)

| Compound | % Number of leaves with Secondary Mildew | Rate of Application |
|---|---|---|
| DINOCAP | 13.2 | 300 ppm |
| No. 5* | 7.4 | 250 ppm |
| No. 8* " | 11.5 | 250 ppm |
| No. 15* " | 4.0 | 250 ppm |

*Dispersible Powder Formulations

TRIAL SERIES NO. 3 (U.K. 1971)
Intensity of Sporulation of Mildew on Primary Mildew Rosettes

| Compound | Rate of Application ppm. | % Mildew Control |
|---|---|---|
| DINOCAP | 300 | 29 |
| BENOMYL | 250 | 36 |
| No. 3* of Table I | 250 | 17 |
| No. 11* of Table I | 250 | 20 |
| No. 5* of Table I | 250 | 32 |
| No. 5** of Table I | 250 | 30 |
| Control | — | 0 |

Secondary Mildew

| Compound | Rate of Application ppm. | % Mildew Control |
|---|---|---|
| DINOCAP | 300 | 38 |
| BENOMYL | 250 | 59 |
| No. 3* (Table I) | 250 | 46 |
| No. 11* (Table I) | 250 | 59 |
| No. 5* " | 250 | 51 |
| No. 5** " | 250 | 66 |
| Control | — | 0 |

*Dispersible powder formulations.
**Contained additional AGRAL wetter.

TRIAL NO. 4 (Spain 1972)

| Compound | Percentage Number of Leaves with Secondary Mildew. | | |
|---|---|---|---|
| | 1st | 2nd | 3rd |
| DINOCAP | 9.1 | 21.3 | 13.3 |
| No. 5* (Table I) | 13.4 | 27.1 | 19.5 |
| No. 8* " | 6.5 | 16.9 | 14.0 |
| No. 15* " | 3.4 | 8.1 | 5.7 |

*Dispersible Powder Formulations.

We claim:

1. A fungicidal composition comprising, as an active ingredient, a fungicidally effective mount of a pyrimidine sulphamate derivative having the formula:

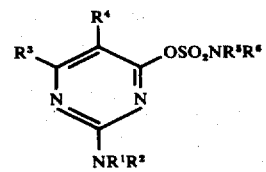

or a salt thereof, wherein $R^1$ and $R^2$ are hydrogen or lower alkyl, lower alkynyl or lower alkenyl but are not both hydrogen, or together with the adjacent N-atom form a monocyclic 5-, 6- or 7-ring atom heterocyclic group, optionally interrupted by an additional hetero atom selected from the group consisting of O, N and S; $R^3$ and $R^4$ are lower alkyl, lower alkynyl or lower alkenyl; and $R^5$ and $R^6$ are lower alkyl, lower alkynyl or lower alkenyl or together with the adjacent N-atom form a monocyclic 5-, 6- or 7-ring atom heterocyclic group, optionally interrupted by an additional hetero atom selected from the group consisting of O, N and S, and a carrier for the active ingredient.

2. A composition according to claim 1 wherein the sulphamate derivative has the formula:

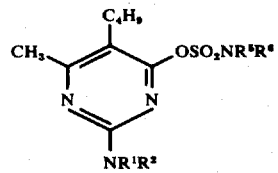

or a salt thereof, wherein $R^1$ and $R^2$ are hydrogen, methyl, ethyl, or allyl, but are not both hydrogen; and $R^5$ and $R^6$ are methyl, ethyl, propyl or butyl or together with the adjacent N-atom form a pyrrolidino, morpholino, piperidino, piperazino or azepino ring, optionally substituted with methyl.

3. A composition according to claim 1 wherein the alkyl and alkenyl groups contain from 1 to 4 carbon atoms, and from 3 to 4 carbon atoms, respectively.

4. A composition according to claim 1 wherein the alkyl groups are methyl, ethyl, propyl or butyl and the alkenyl groups are allyl or butenyl.

5. A composition according to claim 1 wherein the heterocyclic groups are selected from pyrrolidino, morpholino, piperidino, piperazine or azepino rings.

6. A composition according to claim 1 wherein $R_1$, $R_2$ and $R_3$ are methyl, $R_4$ is n-butyl and $R_5$ and $R_6$ form piperidino.

7. A composition according to claim 1 wherein $R_1$, $R_2$ and $R_3$ are methyl, $R_4$ is n-butyl and $R_5$ and $R_6$ form pyrrolydino.

8. A composition according to claim 1 wherein $R_1$, $R_2$ and $R_3$ are methyl, $R_4$ is n-butyl and $R_5$ and $R_6$ form morpholino.

9. A composition according to claim 1 wherein $R_1$ is hydrogen, $R_2$ is ethyl, $R_3$ is methyl, $R_4$ is n-butyl and $R_5$ and $R_6$ form pyrrolidino.

10. A composition according to claim 1 wherein $R_1$ is hydrogen, $R_2$ is ethyl, $R_3$ is methyl, $R_4$ is n-butyl and $R_5$ and $R_6$ are both ethyl.

11. A composition according to claim 1 wherein $R_1$ is hydrogen, $R_2$ is n-propyl, $R_3$ is methyl, $R_4$ is n-butyl and $R_5$ and $R_6$ form pyrrolidino.

12. A composition according to claim 1 wherein $R_1$ is hydrogen, $R_2$ is iso-propyl, $R_3$ is methyl, $R_4$ is n-butyl and $R_5$ and $R_6$ form pyrrolidino.

13. A composition according to claim 1 wherein $R_1$ and $R_2$ are hydrogen or lower alkyl, and $R_3$, $R_4$, $R_5$ and $R_6$ are lower alkyl.

14. A process for combatting fungi which comprises treating plants or seeds with a composition comprising, as an active ingredient, an effective amount of a pyrimidine sulphamate derivative having the formula:

$$\begin{array}{c} R^4 \\ R^3 \diagdown \diagup OSO_2NR^5R^6 \\ | \quad \quad | \\ N \diagdown \diagup N \\ | \\ NR^1R^2 \end{array}$$

or a salt thereof, wherein $R^1$ and $R^2$ are hydrogen or lower alkyl, lower alkynyl or lower alkenyl but are not both hydrogen, or together with the adjacent N-atom form a monocyclic 5-, 6- or 7-ring atom heterocyclic group, optionally interrupted by an additional hetero atom selected from the group consisting of O, N and S; $R^3$ and $R^4$ are lower alkyl, lower alkynyl or lower alkenyl; and $R^5$ and $R^6$ are lower alkyl, lower alkynyl or lower alkenyl or together with the adjacent N-atom form a monocyclic 5-, 6- or 7-ring atom heterocyclic group, optionally interrupted by an additional hetero atom selected from the group consisting of O, N and S.

15. A process according to claim 14 wherein the sulphamate derivative has the formula:

$$\begin{array}{c} C_4H_9 \\ CH_3 \diagdown \diagup OSO_2NR^5R^6 \\ | \quad \quad | \\ N \diagdown \diagup N \\ | \\ NR^1R^2 \end{array}$$

or a salt thereof, wherein $R^1$ and $R^2$ are hydrogen, methyl, ethyl, or allyl, but are not both hydrogen; and $R^5$ and $R^6$ are methyl, ethyl, propyl or butyl or together with the adjacent N-atom form a pyrrolidino, morpholino, piperidino, piperazine or azepino ring, optionally substituted with methyl.

16. A process according to claim 14 wherein the alkyl and alkenyl groups contain from 1 to 4 carbon atoms, and from 3 to 4 carbon atoms, respectively.

17. A process according to claim 16 wherein the alkyl groups are methyl, ethyl, propyl or butyl and the alkenyl groups are allyl or butenyl.

18. A process according to claim 14 wherein the heterocyclic groups are selected from pyrrolidino, morpholino, piperidino, piperazine or azepino rings.

19. A process according to claim 14 wherein $R_1$, $R_2$ and $R_3$ are methyl, $R_4$ is n-butyl and $R_5$ and $R_6$ form piperidino.

20. A process according to claim 14 wherein $R_1$, $R_2$ and $R_3$ are methyl, $R_4$ is n-butyl and $R_5$ and $R_6$ form pyrrolidino.

21. A process according to claim 14 wherein $R_1$, $R_2$ and $R_3$ are methyl, $R_4$ is n-butyl and $R_5$ and $R_6$ form morpholino.

22. A process according to claim 14 wherein $R_1$ is hydrogen, $R_2$ is ethyl, $R_3$ is methyl, $R_4$ is n-butyl and $R_5$ and $R_6$ form pyrrolidino.

23. A process according to claim 14 wherein $R_1$ is hydrogen, $R_2$ is ethyl, $R_3$ is methyl, $R_4$ is n-butyl and $R_5$ and $R_6$ are both ethyl.

24. A process according to claim 14 wherein $R_1$ is hydrogen, $R_2$ is n-propyl, $R_3$ is methyl, $R_4$ is n-butyl and $R_5$ and $R_6$ form pyrrolidino.

25. A process according to claim 14 wherein $R_1$ is hydrogen, $R_2$ is iso-propyl, $R_3$ is methyl, $R_4$ is n-butyl and $R_5$ and $R_6$ form pyrrolidino.

26. A process according to claim 14 wherein $R_1$ and $R_2$ are hydrogen or lower alkyl, and $R_3$, $R_4$, $R_5$ and $R_6$ are lower alkyl.

* * * * *